United States Patent
Muroi et al.

(10) Patent No.: US 8,867,937 B2
(45) Date of Patent: Oct. 21, 2014

(54) DIFFUSE REFLECTION OUTPUT CONVERSION METHOD, ATTACHED POWDER AMOUNT CONVERSION METHOD, AND IMAGE FORMING APPARATUS

(75) Inventors: Hideo Muroi, Kanagawa (JP); Yushi Hirayama, Kanagawa (JP); Shuji Hirai, Tokyo (JP); Hitoshi Ishibashi, Kanagawa (JP)

(73) Assignee: Ricoh Company, Limited, Tokyo (JP)

( * ) Notice: Subject to any disclaimer, the term of this patent is extended or adjusted under 35 U.S.C. 154(b) by 161 days.

(21) Appl. No.: 13/495,405

(22) Filed: Jun. 13, 2012

(65) Prior Publication Data
US 2012/0315056 A1    Dec. 13, 2012

(30) Foreign Application Priority Data
Jun. 13, 2011   (JP) ................................ 2011-131461

(51) Int. Cl.
G03G 15/00 (2006.01)
G01N 21/47 (2006.01)

(52) U.S. Cl.
CPC ........ *G03G 15/5058* (2013.01); *G01N 21/4785* (2013.01); *G03G 2215/0148* (2013.01); *G01N 21/4738* (2013.01)
USPC .............................................. 399/49; 399/74

(58) Field of Classification Search
CPC .......... G01N 21/4738; G01N 21/4785; G93G 15/5058
USPC ...................................... 399/49, 74; 347/131
See application file for complete search history.

(56) References Cited

U.S. PATENT DOCUMENTS

| 7,139,511 | B2 | 11/2006 | Ishibashi | |
| 7,305,195 | B2 | 12/2007 | Ishibashi | |
| 7,382,993 | B2* | 6/2008 | Mongeon et al. ............... | 399/49 |
| 7,398,026 | B2 | 7/2008 | Ishibashi | |
| 7,450,866 | B2* | 11/2008 | Sato ................................ | 399/49 |
| 7,526,219 | B2 | 4/2009 | Ishibashi | |
| 7,546,046 | B2 | 6/2009 | Ishibashi | |
| 7,751,741 | B2* | 7/2010 | Hirai .............................. | 399/74 |
| 7,773,899 | B2 | 8/2010 | Ishibashi | |
| 8,095,025 | B2* | 1/2012 | Ishibashi et al. ............... | 399/49 |
| 2006/0239705 | A1* | 10/2006 | Ishibashi ....................... | 399/49 |
| 2012/0306957 | A1* | 12/2012 | Pawlik et al. | |

FOREIGN PATENT DOCUMENTS

| JP | 5-249787 | 9/1993 |
| JP | 3155555 | 2/2001 |
| JP | 2001-194843 | 7/2001 |
| JP | 2001-324840 | 11/2001 |
| JP | 4456828 | 2/2010 |

* cited by examiner

*Primary Examiner* — Susan Lee
(74) *Attorney, Agent, or Firm* — Oblon, Spivak, McClelland, Maier & Neustadt, L.L.P.

(57) ABSTRACT

In an embodiment, a diffuse reflection output conversion method is executed in an apparatus detecting a plurality of gradation patterns. The apparatus includes a light emitter and light receiver, and detects specular reflection and diffuse reflection simultaneously. A region before specular reflection saturation is a region where the specular reflection component decreases and saturates at minimum level. A diffuse reflection detector is calibrated by: obtaining a diffuse reflection output resulting from an amount of attached powder at a border between the region before specular reflection saturation and the region after specular reflection saturation; calculating a ratio between the diffuse reflection output and a reference diffuse reflection output calculated in advance as a calibration coefficient; and multiplying a diffuse reflection output obtained from the gradation patterns by the calibration coefficient calculated at the calculating.

9 Claims, 10 Drawing Sheets

DIFFUSE REFLECTION OUTPUT CONVERSION METHOD, ATTACHED POWDER AMOUNT CONVERSION METHOD, AND IMAGE FORMING APPARATUS

CROSS-REFERENCE TO RELATED APPLICATIONS

The present application claims priority to and incorporates by reference the entire contents of Japanese Patent Application No. 2011-131461 filed in Japan on Jun. 13, 2011.

BACKGROUND OF THE INVENTION

1. Field of the Invention

The present invention relates to a diffuse reflection output conversion method used in detecting the amount of attached powder, such as toner, an attached powder amount conversion method using the diffuse reflection output conversion method, and an image forming apparatus such as a copier, a printer, a facsimile, a plotter, and a multi-function peripheral (MFP) having at least one of these functions, including a function executing these methods.

2. Description of the Related Art

To achieve a stable image density in a conventional electrophotographic image forming apparatus, such as a copier and a laser beam printer, toner patches (gradation patterns) for detecting density are formed on an image carrier such as a photosensitive element. The density of the patches are detected using an optical detector (hereinafter, also simply referred to as a sensor), and the developing potential is adjusted (specifically, the power of a laser diode (LD), a charging bias, and a developing bias are adjusted) based on the detection result.

As a means for detecting the patches for density detection, reflective sensors are generally known. In a reflective sensor, a light emitting diode (LED) as a light emitter (light emitting means) is combined with a photodiode (PD) or a phototransistor (PTr) as a light receiver (light receiving means).

As types of these sensor, a sensor detecting only a specular reflection illustrated in FIG. 2 (see Japanese Patent Application Laid-open No. 2001-324840, for example), a sensor detecting only a diffuse reflection illustrated in FIG. 3 (see Japanese Patent Application Laid-open No. H5-249787 and Japanese Patent No. 3155555, for example), and a sensor detecting the both illustrated in FIG. 4 (see Japanese Patent Application Laid-open No. 2001-194843, for example) are available.

In FIGS. 2, 3, and 4, the reference numerals 50A, 50B, and 50C represent an element holder. The reference numeral 51 represents an LED, and the reference numeral 52 represents a specular reflection receiver. The reference numeral 53 represents a surface to be detected, the reference numeral 54 represents a toner patch formed on the surface to be detected, and the reference numeral 55 represents a diffuse reflection receiver.

In a sensor having one light emitter and two light receivers illustrated in FIG. 4, characteristics of a diffuse reflection output vary greatly, e.g., due to fluctuations in light emitters and light receivers from different lots, the temperature characteristics and aging of the light emitter and the light receivers, and aging of the transfer belt that is the surface to be detected, as described in Japanese Patent No. 4456828. Therefore, the diffuse reflection receivers need to be calibrated in the manner described below.

A known method for calibrating the diffuse reflection output of a sensor includes drawing gradation patterns, detecting the patterns using a specular reflection receiver that has already been calibrated, obtaining a diffuse reflection output at a reference belt surface exposure ratio from a calculated reference belt surface exposure ratio, which is in one-to-one correspondence with the amount of toner attached, and comparing the actual diffuse reflection output with the reference diffuse reflection output at the reference belt surface exposure ratio. The validity of this calibration method has already been confirmed.

Because a specular reflection output reaches the maximum level on the belt surface, it is known that calibration is performed by adjusting the maximum specular reflection output to a reference specular reflection output.

When area coverage modulation patterns are used for density detection, dot unevenness in a pile height direction and area directions might be present in the half-tone portion.

When analog patterns are used, there might be density unevenness in the patterns as illustrated in FIG. 9, because of a beam pitch variation that could occur in a high-speed unit performing two-beam writing, or banding formed in development.

If such unevenness is present, the belt surface becomes more visible locally, even when the amount attached toner is the same. As a result, the specular reflection output might be increased, and the belt surface exposure ratio might be calculated incorrectly, as illustrated in FIG. 10.

Therefore, the diffuse reflection output cannot be calibrated accurately.

There is need of accurate calibration to be performed in a higher end of the amount of attached powder where dot unevenness or density unevenness is less prominent.

SUMMARY OF THE INVENTION

It is an object of the present invention to at least partially solve the problems in the conventional technology.

In an embodiment, a diffuse reflection output conversion method is executed in an apparatus detecting a plurality of gradation patterns that are formed sequentially on a surface to be detected and each of which is formed with a different amount of attached powder, using an optical detector arranged at a position facing the surface to be detected. The apparatus includes a light emitter and a light receiver, and is configured to detect a specular reflection and diffuse reflections simultaneously. In a relation between a specular reflection output obtained from the gradation patterns and an amount of attached powder, a specular reflection component is a component, in a detected specular reflection output, resulting from a light output from the light emitter and specularly reflected on the surface to be detected; a region before specular reflection saturation is a region where the specular reflection component decreases and saturates at a minimum level; a region after specular reflection saturation is a region where the specular reflection component, in the detected specular reflection output, saturates at the minimum value and remains constant despite the amount of powder attached on the gradation patterns is increased; and a diffuse reflection detector is calibrated by: obtaining a diffuse reflection output resulting from an amount of attached powder at a border between the region before specular reflection saturation and the region after specular reflection saturation; calculating a ratio between the diffuse reflection output and a reference diffuse reflection output calculated in advance as a calibration coefficient; and multiplying a diffuse reflection output obtained from the gradation patterns by the calibration coefficient calculated at the calculating.

In another embodiment, proposed is an attached powder amount conversion method for converting an obtained diffuse reflection output conversion value into an amount of attached powder based on a relation or table data of an amount of attached powder and a diffuse reflection output conversion value, the relation being acquired in advance. The method includes: acquiring the diffuse reflection output conversion value by the diffuse reflection output conversion method mentioned above.

In further embodiment, proposed is an image forming apparatus including a function executing the diffuse reflection output conversion method mentioned above. The method includes using an image carrier, a transfer body, or an intermediate transfer body carrying a recording medium as the surface to be detected, and using toner as the powder.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
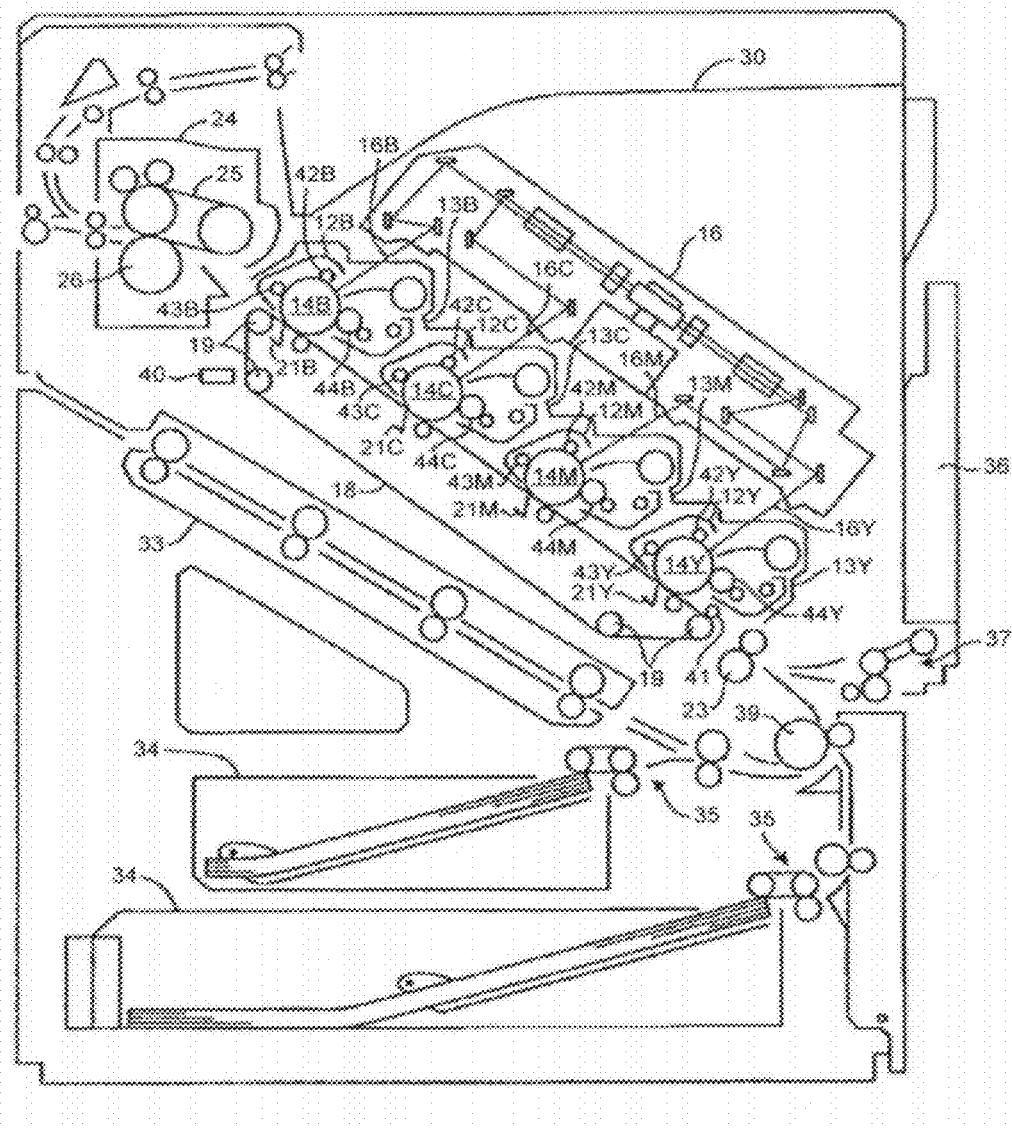
FIG. 1 is a schematic of a general structure of a color laser printer as an image forming apparatus according to an embodiment.
Figure 2:
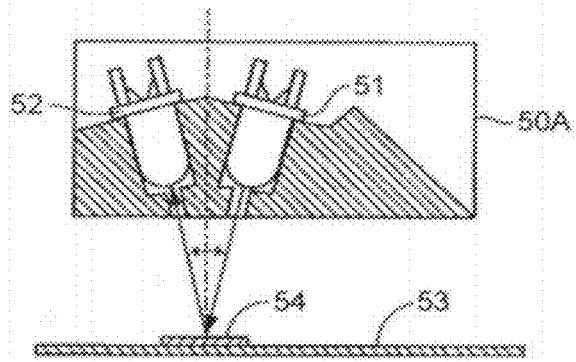
FIG. 2 is a schematic of a structure of an optical detector detecting only a specular reflection.
Figure 3:
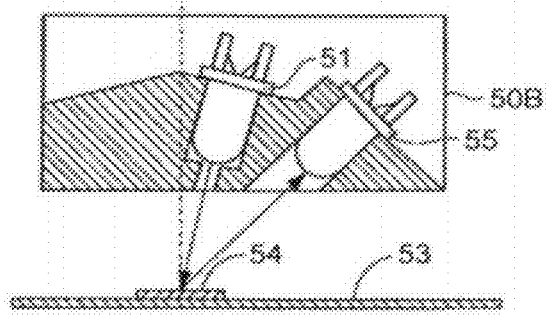
FIG. 3 is a schematic of a structure of an optical detector detecting only diffuse reflections.

An embodiment according to the present invention will now be explained with reference to some drawings.

To begin with, a general structure of a direct transfer, four-drum tandem type color printer that is an image forming apparatus according to the embodiment will now be explained with reference to FIG. 1.

The color laser printer includes three paper feed trays, a bypass tray 36 and two paper feeding cassettes 34 (first paper feed tray) and 34 (second paper feed tray). Paper feeding rollers 37 separate transfer paper, being sheet-like recording media not illustrated, fed from the bypass tray 36 sequentially from the one at the top, and conveys the transfer paper thus separated into a registration roller pair 23.

Paper feeding rollers 35 separate transfer paper fed from the first paper feed tray 34 or the second paper feed tray 34, sequentially from the one at the top, and the transfer paper is then conveyed into the registration roller pair 23 via a pair of carriage rollers 39.

The transfer paper thus conveyed is once stopped and has a skew corrected by the registration roller pair 23, and is further conveyed onto a transfer belt 18 by rotations of the registration roller pair 23 that is caused to rotate by a registration clutch, not illustrated, that is controlled to turn on. The transfer paper is fed onto the transfer belt 18 at timing when the leading end of an image formed on a photosensitive drum 14Y, being a photosensitive drum located most upstream, comes to a position matching a predetermined position of the transfer paper in a conveying direction.

As the transfer paper is passed between a paper attracting nip that is formed between the transfer belt 18 and a paper attracting roller 41 abutting against the transfer belt 18, the transfer paper is attracted onto the transfer belt 18 by an electrostatic force generated by a bias applied to the paper attracting roller 41, and conveyed at a process linear speed of 125 mm/sec.

A transfer bias (positive) at an opposite polarity of charged polarity (negative) of the toner is applied to each transfer brush 21B, 21C, 21M, 21Y arranged facing a corresponding photosensitive drum 14B, 14C, 14M, 14Y, provided for each color, across the transfer belt 18. The transfer bias causes a toner image in each of the colors formed on each of the photosensitive drums 14B, 14C, 14M, 14Y to be transferred onto the transfer paper stuck on the transfer belt 18, sequentially in an order of yellow (Y), magenta (M), cyan (C), and black (Bk).

The transfer paper passed through the transfer process for the respective colors is self-stripped from the transfer belt 18 at the position of a driving roller 19 located downstream, and conveyed into a fixing unit 24.

As the transfer paper is passed through a fixing nip formed between a fixing belt 25 and a pressing roller 26 in the fixing unit 24, the toner image is fixed onto the transfer paper by heat and pressure.

When a simplex printing mode is selected, the transfer paper on which the toner image is fixed is discharged onto a face down (FD) tray 30 provided on top of the image forming apparatus. When a duplex printing mode is selected in advance, the transfer paper coming out from the fixing unit 24 is conveyed into a reversing unit, not illustrated, has its surface reversed by the reversing unit, and is conveyed into a duplex conveying unit 33 located below the transfer unit.

The transfer paper is then fed again by the duplex conveying unit 33, passed through the pair of carriage rollers 39, and carried into the registration roller pair 23.

From that point and thereafter, the transfer paper goes through the same process as that performed in the simplex printing mode, passed through the fixing unit 24, and discharged onto the FD tray 30.

A structure of an image forming operation performed by an image forming unit included in the color laser printer will now be explained.

Because all of the image forming units for these colors have the same structure and perform the same operation, the structure and the operation of the image forming unit forming a yellow image will be explained as an example. For the image forming units for the other colors, reference numerals corresponding to these colors are assigned, and explanations thereof are omitted.

Around the photosensitive drum 14Y that is a photosensitive drum located most upstream in the conveying direction of transfer paper, an image forming unit 12Y having a roller charging device 42Y and a cleaning device 43Y, a developing unit 13Y, an optical writing unit 16, and the like are provided.

Before forming an image, the photosensitive drum 14Y is driven in rotation in a clockwise direction by a main motor not illustrated, and neutralized by an alternating current (AC) bias (with zero direct current (DC) component) applied to the roller charging device 42Y, to have the surface potential neutralized to a reference potential of approximately −50 volts.

A DC bias on which an AC bias is superimposed is then applied to the roller charging device 42Y, to charge the photosensitive drum 14Y uniformly to a potential that is almost equal to the DC component. As a result, the photosensitive drum 14Y is charged to a surface potential of approximately −500 volts to −700 volts (the target charged potential is determined by a process controller).

Digital image information received from a controller not illustrated as an image to be printed is converted into a binary LD output signal corresponding to each color, and the optical writing unit 16 including a cylindrical lens, a polygon motor, an fθ lens, first to third mirrors, and a wide troidal lens (WTL) allows the photosensitive drum 14Y to be irradiated with an exposure light 16Y.

The drum surface potential of the part being irradiated with the exposure light 16Y is reduced to approximately −50 volts. In this manner, an electrostatic latent image corresponding to the image information is formed on the photosensitive drum 14Y.

The developing unit 13Y then visualizes the electrostatic latent image corresponding to yellow image information formed on the photosensitive drum 14Y into a visualized image.

The toner (Q/M: −20 μC/g to −30 μC/g) is developed by applying a DC (−300 volts to −500 volts) on which an AC bias is superimposed to a developing sleeve 44Y in the developing unit 13Y, only in the part of the photosensitive drum 14Y corresponding to the image where the potential is reduced by writing. In this manner, the toner image is formed.

The toner image formed on each of the photosensitive drums 14B, 14C, 14M, 14Y is transferred onto the transfer paper stuck on the transfer belt 18 by the transfer bias.

In addition to the image forming mode described above, the color laser printer according to the embodiment performs a process control operation for adjusting the image density in each color to an appropriate level, which is performed when the image forming apparatus is powered on or after a predetermined number of sheets are passed through the image forming apparatus.

In the process control operation, a plurality of patches for density detection (hereinafter, shortly referred to as "P patterns") are formed on the transfer belt in each color, while changing the charging bias and the developing bias sequentially at an appropriate timing. A density detection sensor (hereinafter, shortly referred to as "P sensor") 40 that is an optical detector arranged outside of the transfer belt 18 near the driving roller 19 is then used to detect the output voltage for each of the P patterns. The output voltage is then converted into an amount of toner attached through an attached amount conversion method (attached powder amount conversion method) according to the embodiments, and the current developing capability (developing γ, Vk) is calculated. Based on the developing capability thus calculated, control is performed to change the developing bias and the control target of the toner density.

Figure 4:
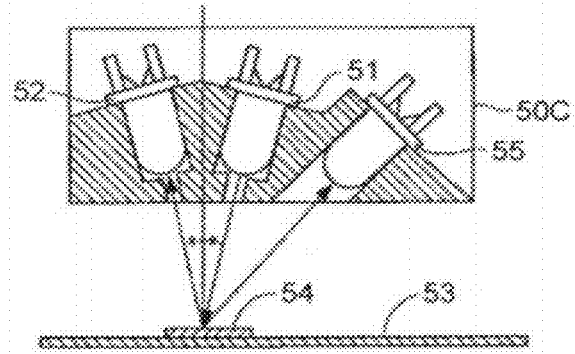
FIG. 4 is a schematic of a structure of an optical detector detecting a specular reflection and diffuse reflections simultaneously.

The structure of the P sensor is as illustrated in FIG. 4, and specifications of the P sensor are as described above.

In this example, a PTr is used as a light receiver, but other light receivers such as a PD may also be used.

Before explaining the embodiment more in detail, challenges in conventional technologies will be explained.

Density Unevenness in Gradation Patterns

In the embodiment, gradation patterns are formed on the transfer belt, and are detected using the P sensor. Because the P sensor outputs almost zero diffuse reflection for the belt, the output cannot be adjusted with respect to the diffuse reflection output for the belt. It could then be considered to perform calibration by adjusting the output with respect to a reference amount of toner attached, but the amount of toner attached on the transfer belt cannot be directly measured.

To overcome this challenge, in the calibration method disclosed in Japanese Patent No. 4456828, a belt surface exposure ratio is defined as a characteristic substituting the amount of toner attached. A calibration is then performed by adjusting the diffuse reflection output acquired at the reference belt surface exposure ratio to a reference diffuse reflection output.

The belt surface exposure ratio is defined as a ratio between a specular component in the reflection from the belt and a specular component in the reflection from the gradation patterns. The "specular component" herein means a specular reflection entering into the specular reflection receiver.

The belt surface exposure ratio of a gradation pattern formed in an amount of powder applied in zero to one layer (hereinafter, referred to as "half-tone") is in a first-order linearity relation with the amount of toner attached. Therefore, by detecting half-tone gradation patterns and adjusting the diffuse reflection output to be calibrated at the reference belt surface exposure ratio to a reference diffuse reflection output, the diffuse reflection output can be calibrated.

However, when area coverage modulation patterns are used for density detections, dot unevenness in a pile height direction and area directions might be present in the half-tone gradation patterns. Even if analog patterns are used instead, there still might be density unevenness in the half-tone gradation patterns as well, because of a beam pitch variation that could occur in a high speed unit performing two-beam writing, or because of banding formed in the development.

Figure 10:
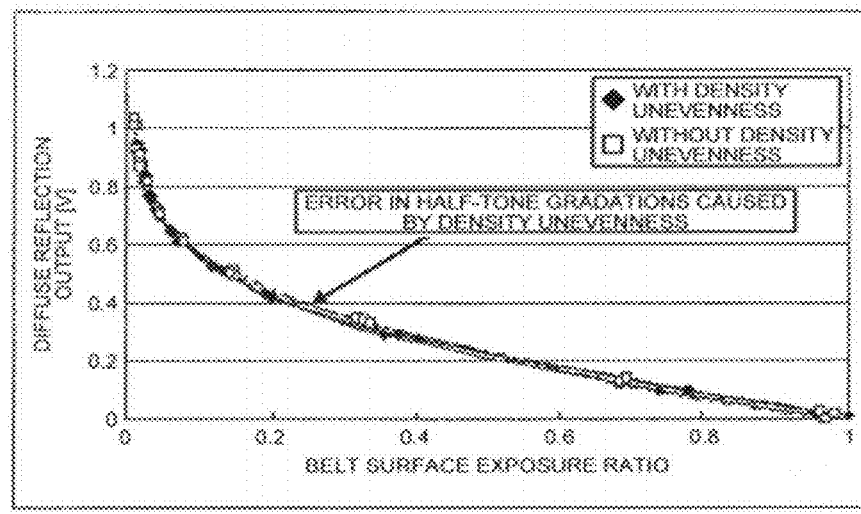
FIG. 10 is a characteristics graph of a change in a corresponding relation between a calculation of a belt surface exposure ratio and the amount of toner attached.
Figure 11A:
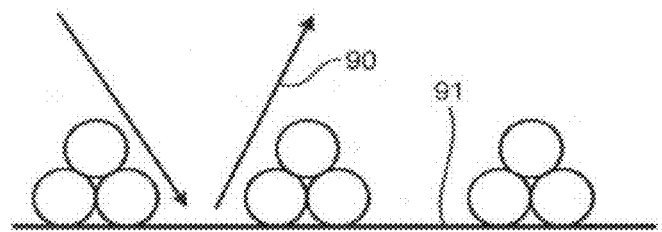
FIGS. 11A and B are schematics illustrating how exposure of the belt changes on surface to be detected when density unevenness is present in half-tone gradation patterns.
Figure 11B:
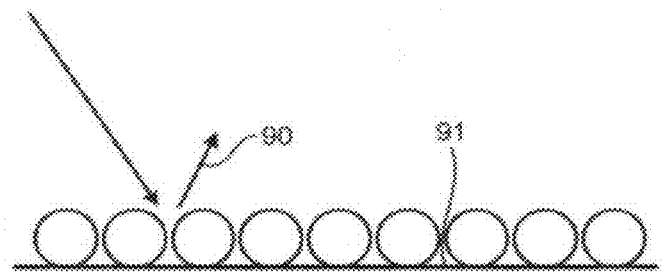

If such unevenness is present, a belt 91 will be exposed more, as illustrated in FIG. 11A, than when the belt 91 is normally exposed as illustrated in FIG. 11B. Such an increase in the exposure might result in an increase in an output for the specular reflection 90 detected for the gradation patterns. The calculated belt surface exposure ratio will then be increased accordingly, as illustrated in FIG. 10, and the relation between the calculated belt surface exposure ratio and the amount of powder attached will be changed. The original intention of adjusting the output at the reference attached amount to the reference output will then no longer be achieved.

In other words, because the conventional technology assumes that the gradation patterns are always formed without any density unevenness, if there is any density unevenness in the half-tone gradation patterns, a calibration error may be added to the diffuse reflection output.

Such a calibration error in the diffuse reflection output directly results in an error in the conversion into an amount of toner attached, and series of control systems involved in image density stabilization may be affected adversely.

The embodiment is made to solve this challenge that has been kept unrevealed in the conventional technology, and to enable calibration of the diffuse reflection output of the P sensor regardless of presence of the density unevenness in the gradation patterns.

This is achieved by a diffuse reflection output conversion method according to the embodiment, an image forming apparatus using the method, and the like.

The diffuse reflection output conversion method according to the embodiment will now be explained. In this method, the calibration is performed avoiding half-tone gradation patterns, by taking advantage of the characteristic of the specular reflection component that becomes zero when the amount of toner attached becomes equal to or more than a certain level.

In this method, the diffuse reflection output is calibrated at following steps:

(1) Sampling a specular reflection output and a diffuse reflection output acquired from gradation patterns;

(2) Acquiring a diffuse reflection output at a border between a region in which the specular reflection component in the detected specular reflection output decreases and saturates at the minimum level as the amount of toner attached on the gradation patterns is increased (region before specular reflection saturation), and a region after the specular reflection component saturates at the minimum level (region after specular reflection saturation); and (3) Taking a ratio between the diffuse reflection output thus acquired and a reference diffuse reflection output acquired in advance as a calibration coefficient, and multiplying the diffuse reflection output acquired from the gradation patterns by the calibration coefficient so as to calibrate the output of the diffuse reflection.

The region before specular reflection saturation can be said to be a region where an increase in the amount of toner attached on the gradation patterns can be detected as a change in the specular reflection component by the specular reflection detector included in the optical detector.

The steps (1) to (3) will now be explained one by one.

Figure 5:
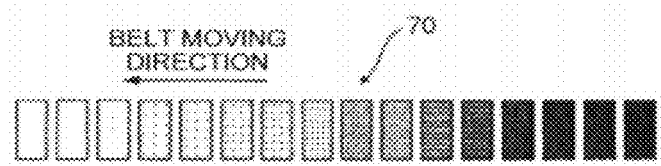
FIG. 5 is a plan view of gradation patterns.

Explanation of Step (1):

As illustrated in FIG. 6, using the P sensor 50 illustrated in FIG. 4, "output voltage for specular reflection" and "output voltage for diffuse reflection" are detected from a P pattern 70 for density detections illustrated in FIG. 5 and formed on the transfer belt 18 illustrated in FIG. 1.

Figure 6A:
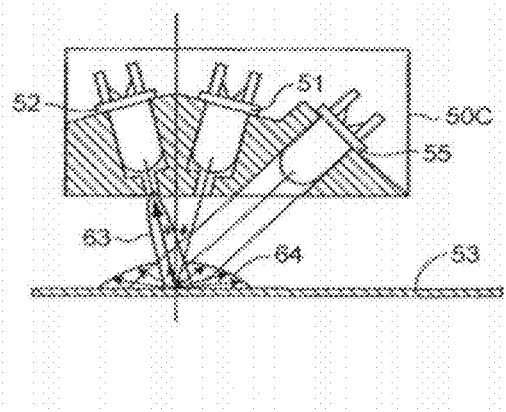
FIGS. 6A and B are schematics illustrating how a diffuse reflection component from a surface to be detected and a diffuse reflection component from a toner layer are included in the light received as a specular reflection by a specular reflection receiver, in addition to a pure specular reflection component.
Figure 6B:
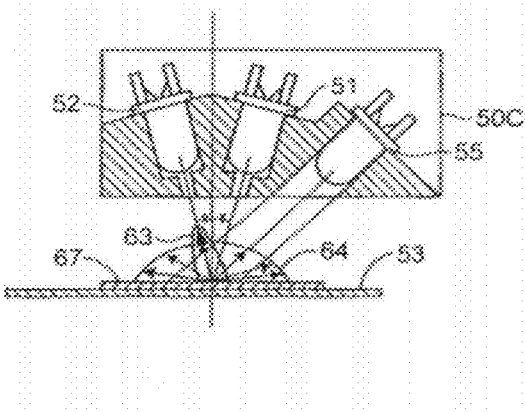
Figure 7:
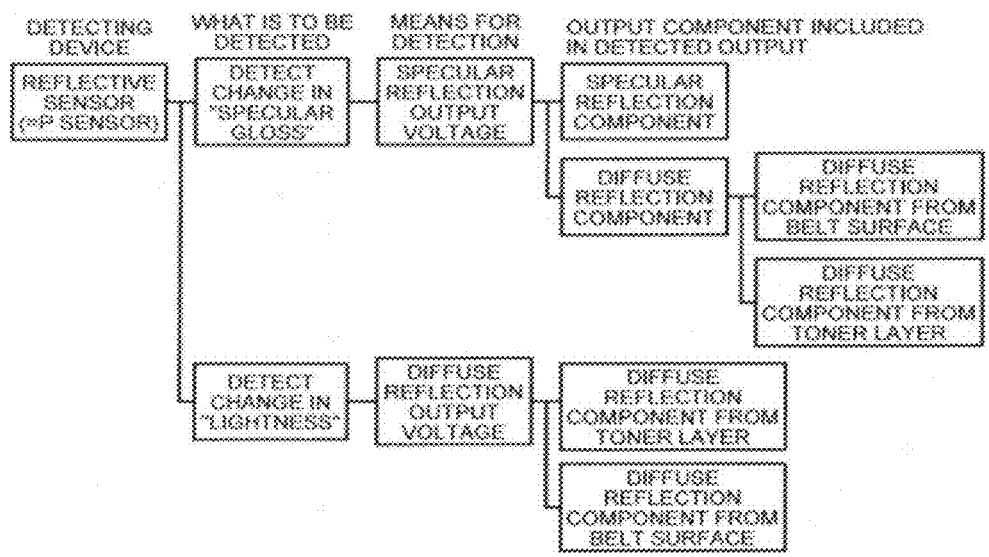
FIG. 7 is a block diagram illustrating a relation between reflection components to be actually detected by an optical detector and reflected light components to be removed.

Explanation of Step (2):

As illustrated in FIGS. 6 and 7, when a light output from LED 51 reaches the belt surface 53 and toner surface 67, the light is speculary and diffusely reflected on each of these surfaces. The light received by the specular reflection receivers 52 contains not only a specular component 63, but also diffuse reflection components 64 reflected from the belt surface and the toner layer. When the belt is exposed in the manner illustrated in FIG. 6A, a higher specular component is received, and when the belt is covered by the toner as illustrated in FIG. 6B, a lower specular component is received.

Figure 8:
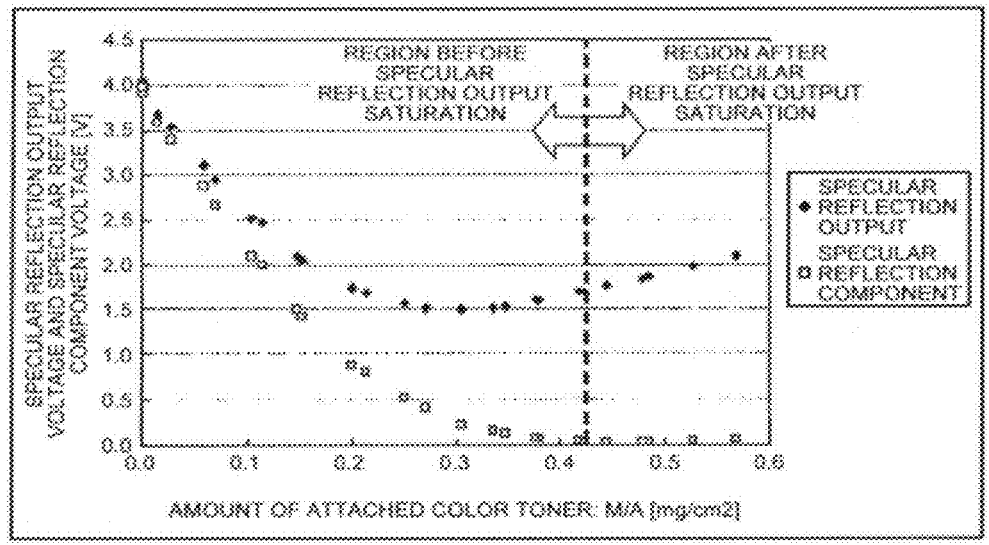
FIG. 8 is a characteristics graph of a region before specular reflection saturation and a region after specular reflection saturation.
Figure 9:
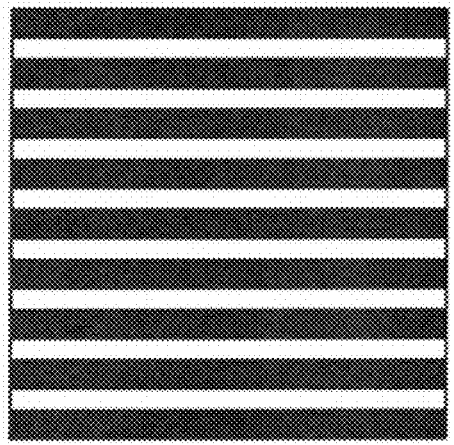
FIG. 9 is a plan view illustrating density unevenness, e.g., caused by banding in development.

As illustrated in FIG. 8, in the region before the specular reflection saturates, as the amount of toner attached increases, the specular reflection component decreases monotonically. This is because, as the belt surface is covered by the toner, a specular reflection from the belt surface decreases. Once the belt surface is completely covered by the toner, any specular reflection is no longer received from the belt surface, and the specular reflection component saturates at the minimum level.

This corresponds to the region after specular reflection saturation. In the region after specular reflection saturation, as the amount of toner attached increases, the specular reflection output keeps increasing even after the specular reflection component is saturated at the minimum level. This is because diffuse reflections from the toner also enter the specular reflection receiver.

The border between the region before specular reflection saturation and the region after the specular reflection saturation comes where all of the lights entering the specular reflection receivers become diffuse reflections.

As to the amount of toner attached at the border, the P sensor used here has been confirmed through experiments not to have any fluctuations attributable to parts, from the view of optical characteristics, and to remain constant regardless of the presence of density unevenness in the half-tone patterns.

Figure 12:
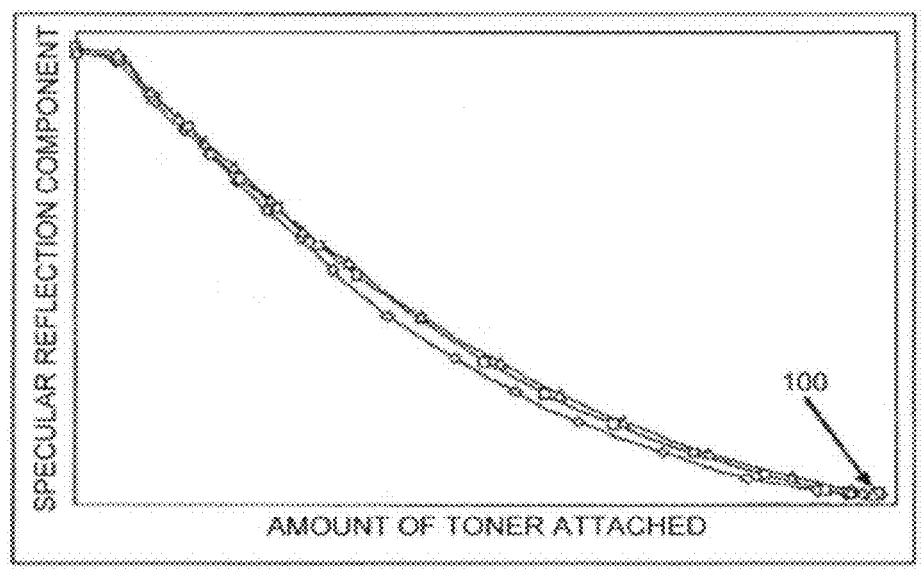
FIG. 12 is a characteristics graph illustrating how the amounts of attached toner are the same at the border.
Figure 13:
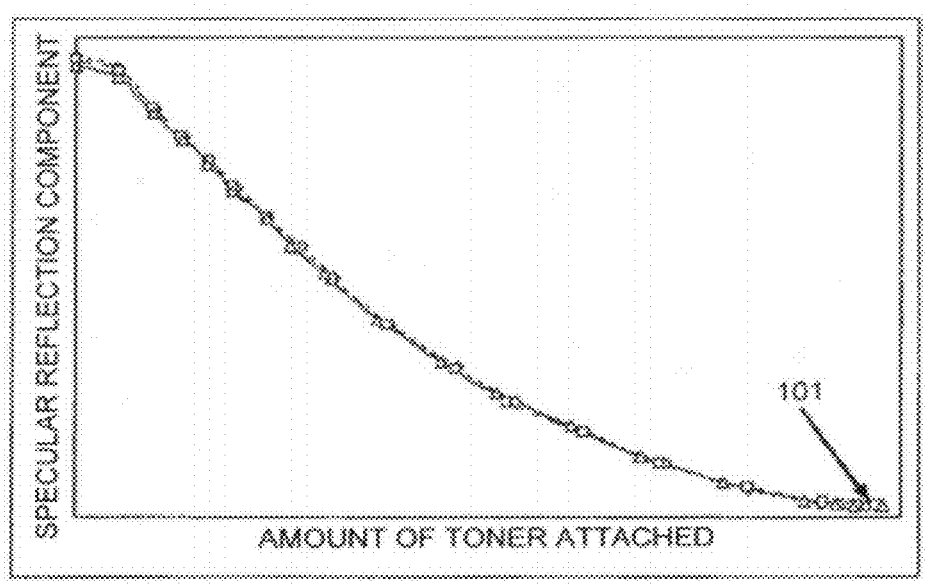
FIG. 13 is another characteristics graph illustrating how the amounts of toner attached are the same at the border.

Example of these characteristics are illustrated in FIGS. 12 and 13. FIG. 12 is a graph plotting the specular reflection component detected and output from a single specular reflection receiver based on three different area coverage modulation patterns having some dot unevenness to the vertical axis, and plotting the measured amount of toner attached to the horizontal axis.

FIG. 13 is a graph plotting the specular reflection component detected and output from three different specular reflection receivers based on three different area coverage modulation patterns with dot unevenness of an equivalent level to the vertical axis, and plotting the measured amount of toner attached on the patterns to the horizontal axis.

In both of these examples, the amount of toner attached was the same at the point 100 or 101 where the specular reflection component saturates.

Therefore, the diffuse reflection output can be preferably calibrated to a reference diffuse reflection output at this point on the border, while avoiding the half-tone regions where the specular reflection component could change.

Figure 14:
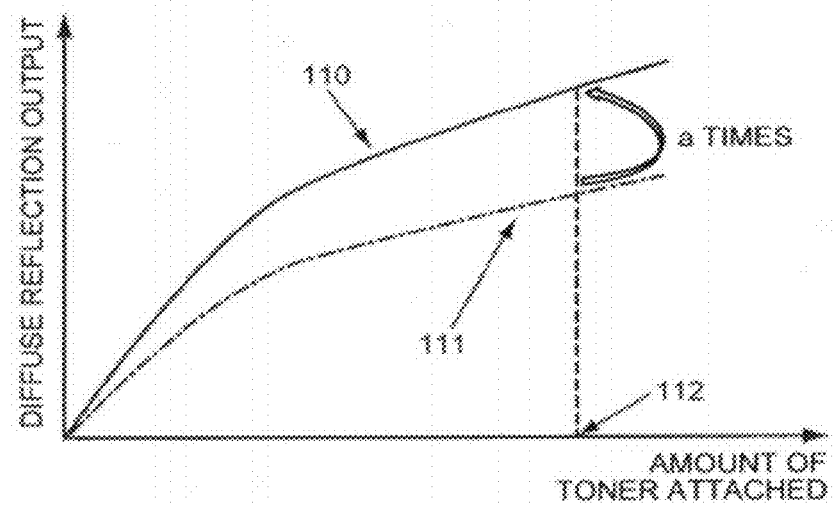
FIG. 14 is a characteristics graph illustrating a ratio between the diffuse reflection output and the reference diffuse reflection output at the border.

Explanation of Step (3):

After calculating the border between the region before specular reflection saturation and the region after specular reflection saturation, a ratio "a" between a diffuse reflection output 111 and a reference diffuse reflection output 110 at the border 112 is obtained, and multiplied by the diffuse reflection output 111 detected from the gradation patterns, in the manner illustrated in FIG. 14.

In this manner, the diffuse reflection output 111 can be calibrated to the reference diffuse reflection output 110.

According to this method, the diffuse reflection output can be calibrated where no fluctuations attributable to parts occur, without using any information of the half-tone portion that is more susceptible to dot unevenness or density unevenness.

The border between the region before specular reflection saturation and the region after specular reflection saturation is determined in the manner described below. In a relation between the specular reflection output and the diffuse reflection output illustrated in FIG. 15, the region before specular reflection saturation is on a line 120 passing the point of origin, and an intersection 122 between near specular reflection saturation characteristics 121 and the line 120 represents the border. Therefore, the intersection 122 is calculated herein. The near specular reflection saturation characteristics can be said to be characteristics near points where the specular reflection component saturates at the minimum level in the specular reflection output.

In this manner, the border can be calculated in a definite manner.

Explained now is how the line passing the point of origin including the region after specular reflection saturation is determined. In the relation between the specular reflection output and the diffuse reflection output acquired from the gradation patterns, as the amount of toner attached increases, the specular reflection component keeps decreasing until it reaches the border between the region before specular reflection saturation and the region after specular reflection saturation, and saturates at the minimum level in the region before specular reflection saturation. By contrast, the diffuse reflection component increases monotonically, as the amount of toner attached increases. The specular reflection receiver receives both of the specular reflection component and the diffuse reflection component, and the diffuse reflection receiver receives only the diffuse reflections.

Figure 15:
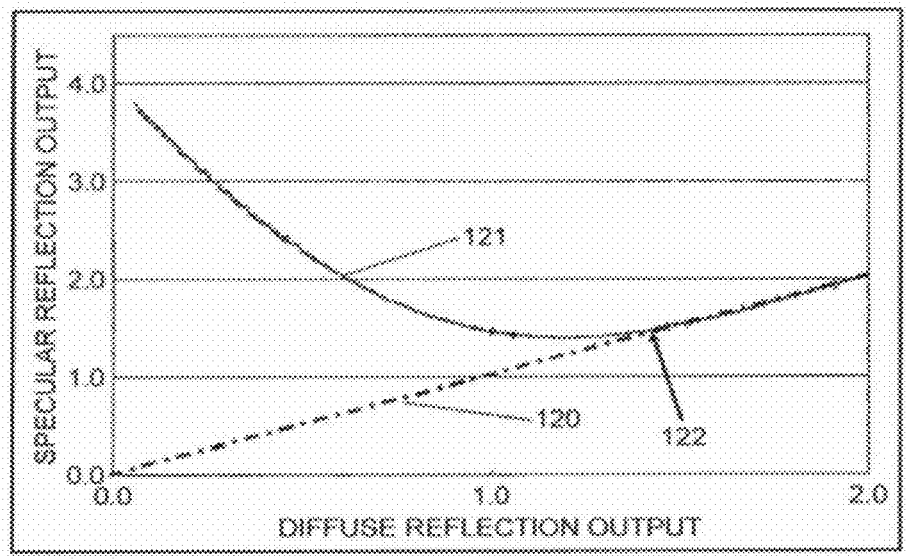
FIG. 15 is a characteristics graph illustrating how the border between the region before specular reflection saturation and the region after specular reflection saturation is determined.

Therefore, by obtaining the ratio between the specular reflection output and the diffuse reflection output, and plotting an approximating line 120 for the samples after the ratio takes the minimum value in the manner illustrated in FIG. 15, the line passing the point of origin including the region after specular reflection saturation can be obtained.

This method has an advantage that the least squares method can be applied to some samples so that measurement fluctuations can be somewhat taken into account, while ensuring the region after specular reflection saturation to be included.

The line passing the point of origin including the region after specular reflection saturation may also be acquired by plotting the approximating line 120 passing the point of origin illustrated in FIG. 15 by using the minimum value of the ratio between the specular reflection output and the diffuse reflection output as the inclination.

This method is effective when it is difficult to obtain the inclination in the manner described earlier because the specular reflection receiver is incapable of receiving the diffuse reflections sufficiently in the region where the amount of toner attached is high.

Figure 16:
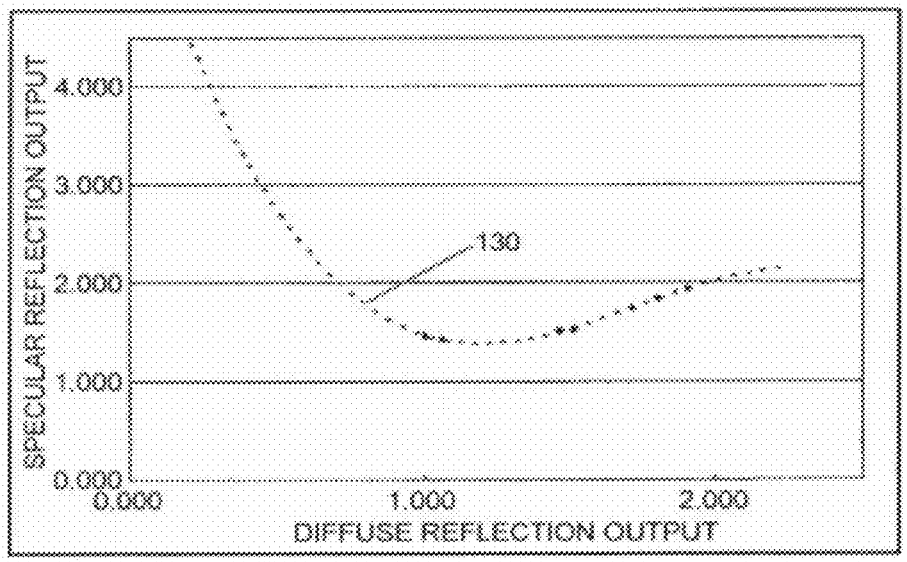
FIG. 16 is a characteristics graph illustrating how near specular reflection saturation characteristics are determined.

As a method for determining the near specular reflection saturation characteristics, a near specular reflection saturation characteristics 130 can be acquired by approximating or interpolating the relation between the specular reflection output and the diffuse reflection output, as illustrated in FIG. 16. In particular, it has been confirmed through experiments that the shape of the entire relation can be expressed and approximated precisely by using a cubic function.

When a quadratic function or a function of lower order is used, approximation errors can be reduced by performing approximation or interpolation only to a limited area near the border between the region before specular reflection saturation and the region after specular reflection saturation.

Figure 17:
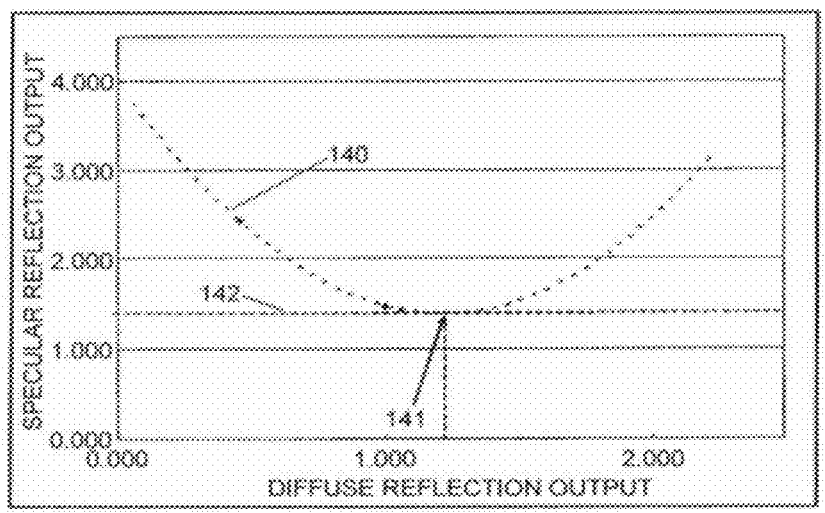
FIG. 17 is a characteristics graph illustrating another example of how near specular reflection saturation characteristics are determined.

Explained below is another method for determining the near specular reflection saturation characteristics. As illustrated in FIG. 17, a quadratic approximation 140, for example, is performed using data of the region before specular reflection saturation and the region after specular reflection saturation to calculate a minimum value 141 of the specular reflection output. It is assumed herein that the output saturates and does not increase or decrease over a certain interval from the minimum value 141 toward the higher end of the amount of toner attached.

Assuming that the region after specular reflection saturation appears immediately after the saturation, a line 142 passing the minimum value 141 at zero inclination can be used as the near specular reflection saturation characteristics.

This method is effective when it is difficult to obtain the inclination in the manner described earlier because the specular reflection receiver is incapable of receiving the diffuse reflections sufficiently in the region where the amount of toner attached is high, and it is difficult to acquire the border in the method explained in FIG. 16.

Figure 18:
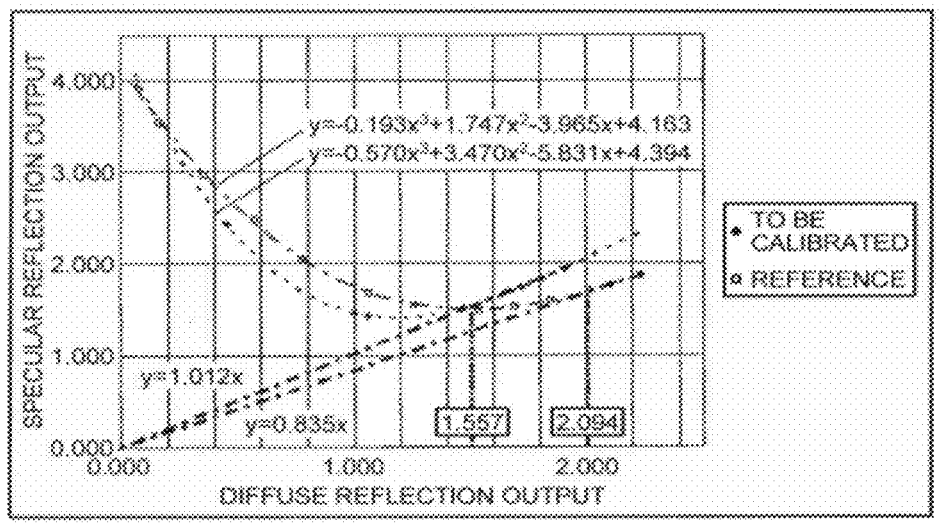
FIG. 18 is a characteristics graph for explaining how a calibration coefficient is calculated with some specific exemplary numbers.

Typical examples of numbers according to the embodiment are represented in FIG. 18. In FIG. 18, the specular reflection output is denoted by y, and the diffuse reflection output is denoted by x. A plurality of gradation patterns were formed sequentially on the surface to be detected, with different amounts of attached powder, and calibration is performed using these gradation patterns.

The border for the reference P sensor is calculated in advance based on experiments. In the embodiment, the border for the reference P sensor is calculated based on experiment data conducted in advance. Therefore, the data presented in items in the calculations of the border for the reference P sensor are already known.

1. Calculating Border for Reference P Sensor (1): Calculate the region after specular reflection saturation using the least squares method.

$y=0.835x$ (2): Perform a cubic approximation of data points using the least squares method, to acquire approximation characteristics in the area near the border.

$y=-0.193x^3+1.747x^2-3.965x+4.163$ (3): Calculate the diffuse reflection output at the intersection (border) between (1) and (2) using the steepest descent method, for example.

$x=2.094$

2. Calculating Border for P Sensor to be Calibrated (1): Calculate the region after specular reflection saturation using the least squares method.

$y=1.012x$ (2): Perform a cubic approximation of data points using the least squares method, to acquire approximation characteristics in the area near the border.

$y=-0.570x^3+3.470x^2-5.831x+4.394$ (3): Calculate the diffuse reflection output at the intersection (border) between (1) and (2) using the steepest descent method, for example.

$x=1.557$

3. Calculate Calibration Coefficient $a=2.094/1.557=1.345$

The calibration is completed by multiplying the diffuse reflection output of the P sensor to be calibrated by the calibration coefficient an obtained in the manner described above.

Examples of numbers according to methods other than that according to the embodiment are omitted.

Figure 19:
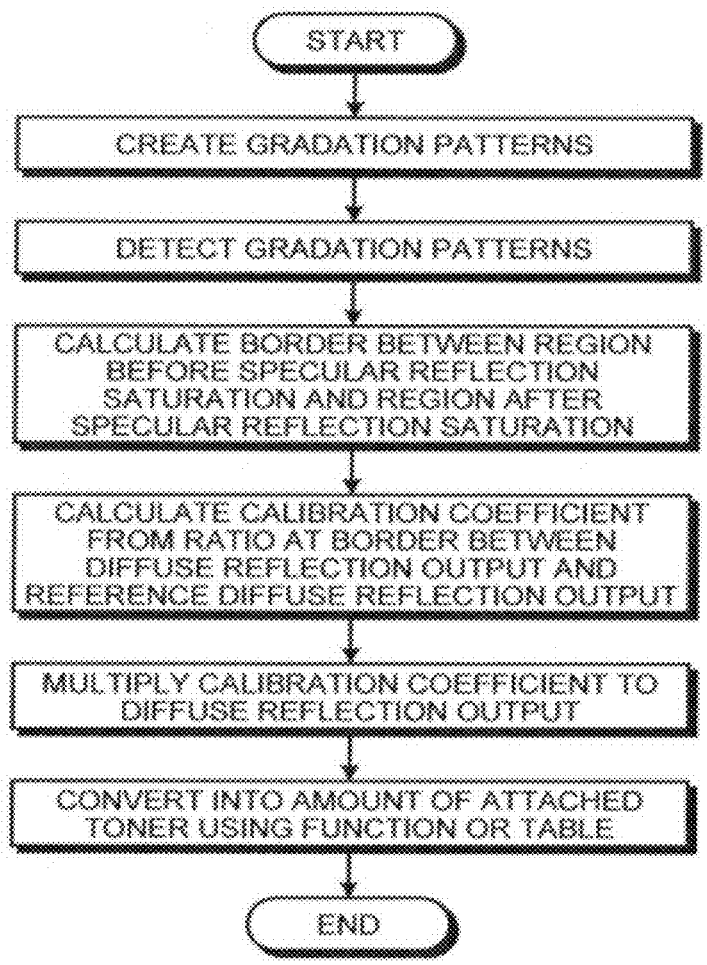
FIG. 19 is a flowchart of a process of an attached powder amount conversion method.

After the calibration is completed, a diffuse reflection output can be converted into the amount of attached powder based on a relational equation or table data of the amounts of attached toner and post-calibration diffuse reflection outputs prepared in advance. The process of converting the diffuse reflection output into the amount of attached powder is illustrated in FIG. 19.

Even after the calibration is completed, the diffuse reflection output conversion or the attached powder amount conversion may be performed by multiplying a diffuse reflection output obtained from certain patterns by the calibration coefficient obtained through the diffuse reflection output conversion method.

The diffuse reflection output conversion method may be used in an image forming apparatus using toner, or in a detector of the amount of attached powder.

According to the embodiment, by avoiding the half-tone section where dot unevenness or density unevenness is more prominent, the diffuse reflection output of a sensor can be calibrated from a higher end of the amount attached toner, and calculation of the amount of attached powder can be improved. This can facilitate improvement in image quality.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A diffuse reflection output conversion method, comprising detecting, via an apparatus, a plurality of gradation patterns that are formed sequentially on a surface to be detected and each of which is formed with a different amount of attached powder;

using an optical detector arranged at a position facing the surface to be detected, the optical detector including a light emitter and a light receiver, and being configured to detect a specular reflection and diffuse reflections simultaneously, wherein in a relation between a specular reflection output obtained from the gradation patterns and an amount of attached powder, a specular reflection component is a component, in a detected specular reflection output, resulting from a light output from the light emitter and specularly reflected on the surface to be detected, a region before specular reflection saturation is a region where the specular reflection component decreases and saturates at a minimum level, a region after specular reflection saturation is a region where the specular reflection component, in the detected specular reflection output, saturates at the minimum level and remains constant despite an increase in the amount of powder attached on the gradation patterns, and a diffuse reflection detector is calibrated by:

obtaining a diffuse reflection output resulting from an amount of attached powder at a border between the region before specular reflection saturation and the region after specular reflection saturation, calculating a ratio between the diffuse reflection output and a reference diffuse reflection output calculated in advance as a calibration coefficient, and multiplying a diffuse reflection output obtained from the gradation patterns by the calibration coefficient calculated at the calculating.

2. The diffuse reflection output conversion method according to claim 1, wherein the border between the region before specular reflection saturation and the region after specular reflection saturation is calculated, in a relation between the specular reflection output and the diffuse reflection output acquired from the gradation patterns, from an intersection between a relation between a specular reflection output and a diffuse reflection output with being a first-order linearity relation passing a point of origin and a near specular reflection saturation characteristic where the specular reflection output decreases, saturates, and increases as the diffuse reflection output increases.

3. The diffuse reflection output conversion method according to claim 2, wherein an inclination of the first-order linearity relation passing the point of origin is calculated based on a plurality of points, in the relation between the specular reflection output and the diffuse reflection output, on a side where a level of the diffuse reflection output becomes higher with respect to a point where a ratio between the specular reflection output and the diffuse reflection output takes a minimum level.

4. The diffuse reflection output conversion method according to claim 2, wherein an inclination of the first-order linearity relation passing the point of origin is a minimum level of a ratio between the specular reflection output and the diffuse reflection output.

5. The diffuse reflection output conversion method according to claim 2, wherein the near specular reflection saturation characteristic is an approximating characteristic obtained by applying approximation or interpolation to the relation between the specular reflection output and the diffuse reflection output.

6. The diffuse reflection output conversion method according to claim 2, wherein the near specular reflection saturation characteristic is represented as a line with zero inclination passing the minimum specular reflection output in a region before the specular reflection saturation, or the specular reflection output of an approximating characteristic of the region before specular reflection saturation being at a minimum level.

7. The diffuse reflection output conversion method according to claim 1, wherein after the calibration is completed, a post-calibration output is obtained by detecting certain powder patterns formed on the surface to be detected, and by multiplying a diffuse reflection output detected with the calibration coefficient.

8. An attached powder amount conversion method for converting an obtained diffuse reflection output conversion value into an amount of attached powder based on a relation or table data of an amount of attached powder and a diffuse reflection output conversion value, the relation being acquired in advance, comprising:

acquiring the diffuse reflection output conversion value by the method according to claim 1.

9. An image forming apparatus that executes the method according to claim 1, the apparatus comprising:

an image carrier, a transfer body, or an intermediate transfer body carrying a recording medium as the surface to be detected; and toner as the powder.

* * * * *